United States Patent

Ibsen et al.

[11] 4,117,595
[45] Oct. 3, 1978

[54] METHOD FOR REPAIR OF PORCELAIN DENTAL PROSTHESES

[75] Inventors: Robert L. Ibsen; William Richard Glace, both of Santa Maria, Calif.

[73] Assignee: Den-Mat, Inc., Santa Maria, Calif.

[21] Appl. No.: 787,754

[22] Filed: Apr. 15, 1977

[51] Int. Cl.² .............................................. A61C 13/00
[52] U.S. Cl. .............................................. 32/8; 32/1
[58] Field of Search .................. 264/16, 18; 32/8, 15, 32/1

[56] References Cited

U.S. PATENT DOCUMENTS

| | | | |
|---|---|---|---|
| 2,558,139 | 6/1951 | Knock et al. | 264/16 |
| 3,400,097 | 9/1968 | Weinstein et al. | 32/8 |
| 3,986,261 | 10/1976 | Faunce | 32/15 |

Primary Examiner—Louis G. Mancene
Assistant Examiner—John J. Wilson
Attorney, Agent, or Firm—Owen, Wickersham & Erickson

[57] ABSTRACT

A kit containing the components essential for repairing, in situ, damaged or fractured porcelain dental prostheses. A method for carrying out such repair includes cleaning, shaping, and priming the damaged area, applying a bonding agent preferably containing two silanes and a water-displacing solvent, then applying a filling agent comprising vitreous powder and a resin binder, allowing the agent to set and harden, and finishing. A filler composition or agent and an advantageous bonding composition are also provided.

7 Claims, 7 Drawing Figures

U.S. Patent   Oct. 3, 1978   Sheet 1 of 2   4,117,595
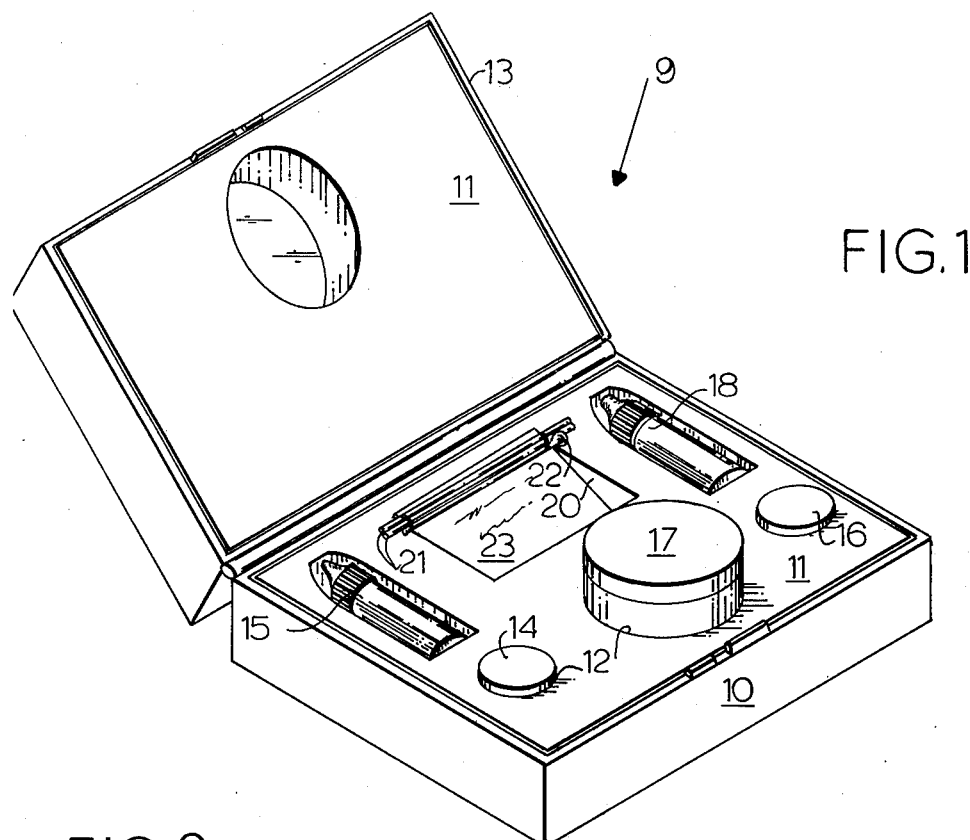
FIG.1
FIG.2
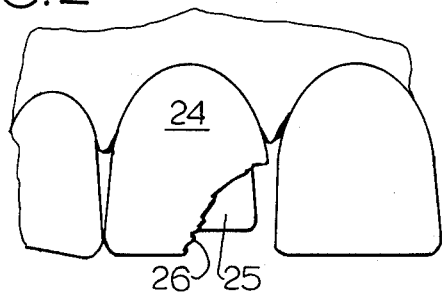
FIG.3
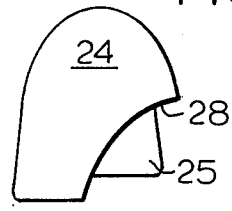
FIG.4
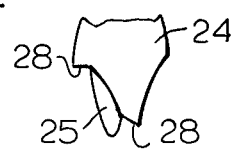
FIG.5
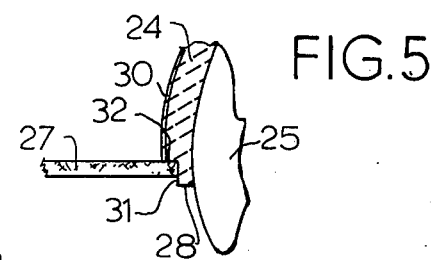
FIG.6
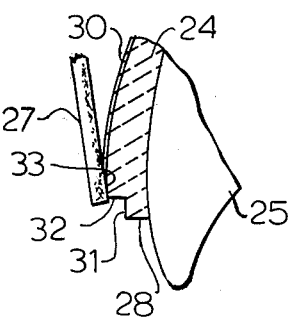

METHOD FOR REPAIR OF PORCELAIN DENTAL PROSTHESES

BACKGROUND OF THE INVENTION

This invention concerns a kit for repairing damage to, and for restoring, damaged porcelain dental prostheses, such as porcelain caps or other previous restorations; and the invention concerns a method for making such repairs, and a composition for making such repair.

Porcelain dental prostheses are rather brittle, and they are often fractured or even partially broken off by accident or by improper use by the wearer or by stresses caused by the wearer's mastication. When this has happened, particularly, of course, with a fixed prosthesis or crown, it has heretofore been first necessary to remove the damaged prosthesis or crown. A new prosthesis was then prepared, and it was replaced in the patient's mouth at a later date. This tedious, time-consuming and expensive procedure was irksome and inconvenient for the patient, and it generally required an anesthetic.

The present invention provides a kit for repair of such damaged prosthesis while it remains in the patient's mouth. This kit contains all of the components necessary to make such repair in situ, using as tools the customary or available tools of the art. The kit is advantageous because the damaged area can be quickly prepared for repair by, first, cleaning and smoothing the damaged surfaces, while providing perpendicular walls at the site. Then the filling component of the kit is prepared and placed in the cavity in the damaged porcelain, allowed to set, and then finished. The whole operation normally is carried out in about 12 minutes.

Another advantage of the present invention is that no glazing of the finished repair is necessary, although glazing can be effected, if desired. The kit of this invention is easy to use, is compact, and can provide excellent shading of the repaired area to match the surrounding teeth or dentures. The method and mixing techniques of this invention are simple and are easily carried out. The filler component obtainable with the kit of this invention can provide excellent shading, as noted. It also adapts well into the walls of the prepared surface and adapts well to prepared margins of such surface, so that the filling or restoration is easy to finish.

A porcelain dental restoration typically comprises a metal base or jacket over the tooth itself, and the porcelain is applied as a coating of the desired thickness overlying and strongly bonded to the outer surface of the metal jacket.

The invention incorporates a system and materials for opaquing out the metal base in instances where the damage exposes bare metal.

A further advantage is that the kit provides restoration components which will set to a hard finish within times adapted to the individual dentist's practice requirements. It is another advantage that the kit does not contain cyanoacrylate, which tends to decompose in the body.

SUMMARY OF THE INVENTION

The invention provides a kit for repair of damaged dental porcelain restorations. The kit contains at the least, a priming agent, an adhesive or bonding agent, a restorative material, an opaquing agent for metal substrate, and plastic mixing and applying means. The invention also concerns an advantageous restorative material for repair of such restorations in situ and a method for carrying out such repair.

The priming agent in the kit is applied to the damaged area of the restoration after it has been thoroughly cleaned and mechanically prepared, as will be described below. The priming agent is an aqueous solution of a weak acid, such as dilute citric acid, or phosphoric acid, or other innocuous acid. Citric acid, for example, is not harmful for use in a patient's mouth, and is, in aqueous solution, an effective as well as safe priming agent. An advantageous priming agent consists essentially of water and from 1 to 60% by weight of the solution of citric acid, preferably about 30% thereof. Where the metal substrate is exposed, it is believed that the priming agent temporarily alters the surface energy of the metal surface and results in stronger bonding between the metal and the porcelain overlay.

The bonding agent of the kit comprises a mixture of a plurality of silanes and a solvent, preferably one which is also a water-displacement agent. The surface water is substantially impossible to remove completely by air drying or other normal means available at the temperatures and under the normal working conditions encountered by the dentist. Thus, it is quite advantageous to use a liquid water-displacing agent, which upon contact of a drop of such agent with the surface water will force the water outward in a circular path to form a small area of the substrate surface which is quite water-free. Butanol may be employed as the solvent for the silanes, for it is also a water-displacement agent. That is, when butanol is placed in contact with the thin residual layer of water (which is always present at the surface of the metal base and the original porcelain walls), butanol displaces the water and gives the silanes immediate access to the metal and walls, to which the silanes will then bond. Additionally, butanol has a low vapor pressure at the temperature of working, which affords time for the surface hydrolysis of the silanes, that is, hydrolysis of the silanes by the surface water, and subsequent attachment of the silane bond to the ceramic substrate. Butanol is the preferred liquid or solvent, and it contains in solution from 0.5 to 25%, preferably about 5%, by weight of the solution of gamma-methacryloxypropyltrimethoxysilane, (A-174),

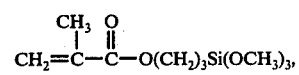

and from 0.25 to 12%, preferably about 2.5%, of gamma-glycidoxypropyltrimethoxysilane, (A-187),

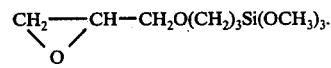

The restorative material of the kit or system comprises two components, namely, a vitreous white powder and a binder. The vitreous powder is of particle size normally used in forming dental restorations, for instance, passing through 325 mesh. The powder may be made as follows:

| Ingredient | Parts by Weight |
|---|---|
| 1. Kimble Ray-Sorb T-2000 glass | 30 |
| 2. Kimble Cer-Vit T-1000 glass | 65 |
| 3. Amorphous Silica | 5 |
| 4. Coupling agent, e.g., A-174 silane | 1.5 |
| 5. Cure initiator for resin, e.g., | |

| Ingredient | Parts by Weight |
| --- | --- |
| benzoyl peroxide | 1.5 |

Ingredients 1, 2, and 3 may consist of almost any combination of glasses and/or silicas including quartz, borosilicate glass, etc. Ingredients 4 and 5 may vary by as much as ±100% for each. If ultra-violet curing is to be done, ingredient 5 can be omitted.

The binder is a resin which is cold-setting and is compatible with the environment of the mouth. A diluted ethoxylated bisphenol A dimethacrylate resin is an excellent binder for the porcelain powder. This compound also appears to improve bonding of the filler to the substrate. The resin, which contains suitable diluents, anti-oxidants, and stabilizers, is used in the proportion of about one part by weight to three to four parts by weight of the vitreous powder. The consistency of the mix is most important. It should be wet but just barely too thick to flow. An example of a suitable resin is as follows:

| | Ingredient | Parts by Weight |
| --- | --- | --- |
| 1. | Ethoxylated bis-phenol A dimethacrylate | 80 parts |
| 2. | triethylene glycol dimethacrylate | 20 parts |
| 3. | 2-hydroxy-4-methoxy-benzophenone | 2 parts |
| 4. | butylated hydroxy-toluene | 0.05 parts |
| 5. | 2-hydroxy-ethyl p-toluidine | 0.30 parts |

The relative proportions of ingredients 1 and 2 of the resin may vary from 100:40 to 0:60. Other well-known dental restorative resins of suitable type may be used. The other three components may vary by as much as ±100% for each, and each may be any of a series of such compounds:

3. is an ultra-violet absorber.
4. is an anti-oxidant and free-radical scavenger.
5. is an aromatic tertiary amine accelerator.

Ingredient 5 can be replaced by a suitable ether (methyl benzoin ether) for curing by ultra-violet light.

The metal opaquer of the kit functions to coat any exposed surface of the metal base of the prosthesis in the damaged area, in order to avoid translucency and local discoloration of the restored portion. The metal opaquer is a vitreous powder, suitably a mixture of particle sizes from about 2 to about 95 microns and having sufficient added pigment, such as titanium dioxide, to render it opaque. For use in masking the metal, this powder is mixed with the same resin as is used to prepare the filler agent as above, and in the same amount.

In the method according to this invention the fractured or damaged area of the restoration is given a preliminary cleaning treatment, whereby the surrounding area or surface of the porcelain is polished with pumice and water to remove any plaque contamination and then all weak portions of porcelain removed. Perpendicular walls are then established, and a shoulder or set-back is formed at about one-half the depth of the thickness from the metal base to the outer surface of the porcelain. Also, a small amount of surface glaze is removed to obtain maximum mechanical advantage. Thus far, there is no call upon the kit. The dentist uses traditional tools and materials.

The damaged area is then treated with a priming agent such as described above, after which the priming agent is removed with a water rinse and air blast. Thereafter, the bonding agent is applied to the dried area and allowed to remain in place for at least twenty seconds. The bonding agent can be allowed to stand for a longer time, up to an hour even, but in practice, the restoration usually proceeds after waiting only twenty to thirty seconds. Any excess solution remaining is then removed by a gentle air blast, and the metal opaquing agent is applied to any metal surface which may be exposed.

During the waiting period for the bonding agent, the restoring agent may be prepared by mixing the resin and vitreous powder in such relative amount that the mixture is wet but just barely too thick to flow, all as described above. The mixture is quickly applied to the damaged area, with a suitable instrument, preferably of inert material such as a plastic, such an instrument being, preferably, furnished with the kit. The mixture should be applied in small increments to prevent running.

The restored area is allowed to set for six to seven minutes and is then ground with standard cuttlefish disks and fine diamonds for gross finishing. For final finishing rubber wheels or any desired finishing paste can be used. Suitably, thereafter, a glazing agent is then applied to obtain a smooth surface.

The kit, including the filler and bonding agents, should be stored in a cool, dry place for extended shelf life.

BRIEF DESCRIPTION OF THE DRAWINGS

In the Drawings:

The annexed drawings represent some embodiments which illustrate modes of carrying out the present invention:

FIG. 1 is a view in perspective of one arrangement of a basic kit embodying the principles of the present invention.

FIG. 2 is a front view of a broken porcelain crown on an incisor in a patient's mouth.

FIG. 3 is a front view of the damaged crown and tooth only, of FIG. 2, with weak and friable portions removed.

FIG. 4 is a view in side elevation of the damaged area of the tooth of FIG. 3.

FIG. 5 is a sectional view of the front portion of the damaged area of the tooth of FIG. 3.

FIG. 6 is a sectional view of a front portion of the damaged area of the tooth of FIG. 3, showing another embodiment of the side wall preparation.

DETAILED DESCRIPTION OF THE INVENTION

Figure 7:
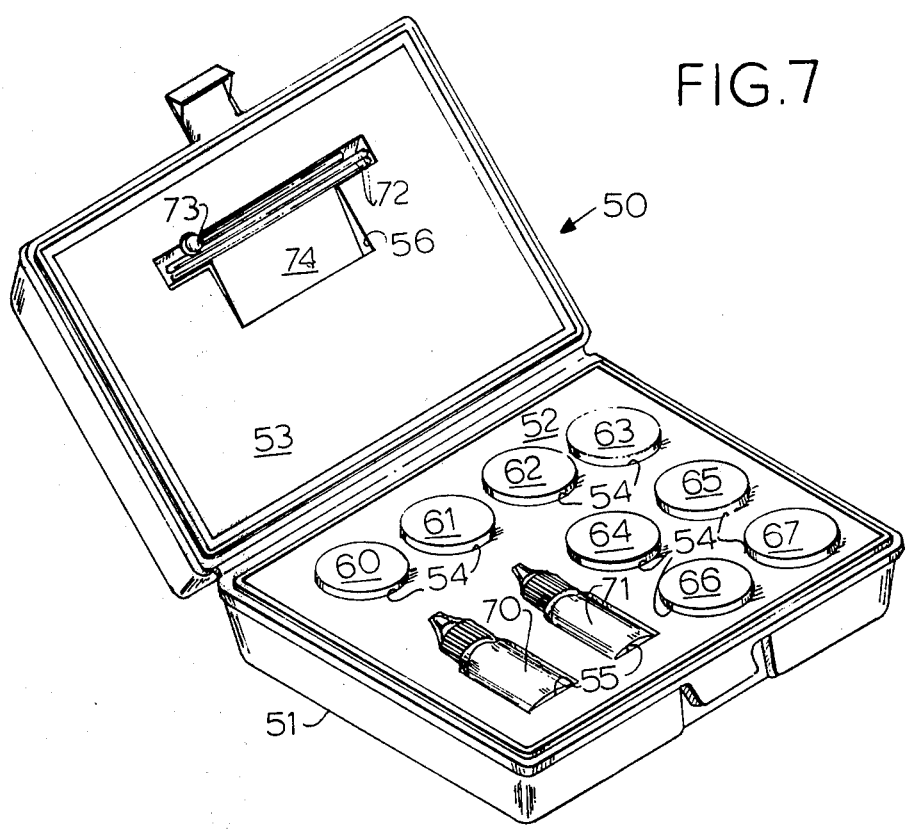
FIG. 7 is a view in perspective of another form of kit embodying the principles of the invention.

A kit 9 of the present invention is shown in perspective in FIG. 1, wherein a box or container 10, in this instance of plastic, is fitted with a cushioning liner 11 which can be foamed plastic or resin and which has suitable recesses or depressions 12. The container 10 preferably has a hinged lid 13. In this box 10 are placed (1) a small closable container 14 filled with priming agent, (2) a plastic squeeze bottle 15 containing the bonding agent for placement on the cleaned surfaces of the damaged area of a prosthesis, (3) a second closable container 16 filled with metal opaquing powder, (4) a third closable container or box 17, suitably larger than the boxes 14 and 16 and enclosing an amount of vitreous white powder, and (5) a second squeeze bottle 18 containing resin binder for forming a restoring material in admixture with the vitreous powder in the box 17. Each of these bottles, boxes, or containers 14 through 18 is disposed and protected in its own depression or recess 12 in the liner 11. Additionally, in another recess 20, there are placed (6) a couple of plastic tools 21 for mixing and, if desired, applying the restorative material, (7) a handled scoop 22 for measuring an amount of vitreous powder in preparing the powder-resin mixtures, and suitably, (8) a packet of liquid-resistant slips of paper 23 for the dentist's convenience in mixing the vitreous powder restorative material.

To illustrate one mode of carrying out the method of this invention, for example, a damaged porcelain restoration is shown in FIGS. 2 through 6. A porcelain jacket or crown 24 has been broken off at one corner, exposing a gold base or tooth substrate 25 and exhibiting a weak, jagged edge 26.

In a first step, the area of the porcelain surrounding the damaged zone is polished with pumice and water to remove any plaque contamination. Then a high-speed diamond-stone tool 27 is used to remove friable porcelain, leaving a clean regular perpendicular wall 28. An additional 2 to 3 mm is then removed, to a depth of one-half the thickness of the porcelain between its surface 30 and the gold substrate 25, forming a set back or shoulder 31 having also a perpendicular wall 32, suitably using the diamond stone also. The shoulder 31 is approximately parallel to the surface 30 of the porcelain jacket or crown 24. The diamond tool 27 is also employed to remove a small amount, about 1 mm, of surface glaze 33 in order to obtain maximum mechanical advantage, that is, strongest bonding of filler to the porcelain jacket or crown 24.

After the above shaping has been accomplished, the damaged area is cleaned by applying the priming agent, which is an aqueous solution of a weak acid. In this example, the priming agent is a 30% by weight solution of citric acid in water. The priming agent can be applied with a cotton pellet and then should be removed with a water rinse and an air blast.

Bonding agent is then applied to the damaged area with a cotton pellet. The bonding agent preferably comprises a solution of about 5% by weight of a silane available under the trade designation A-174, which is gamma-methacryloxypropyltrimethoxysilane, and about 2.5% by weight of another silane available under the trade designation A-187, which is gamma-glycidoxypropyltrimethoxysilane (both of these silanes being products of Union Carbide Corporation); the remainder is the solvent, butanol. The butanol displaces any water remaining or existing on the surfaces of the metal and of the porcelain and enables the silanes to be sufficiently hydrolyzed by such water to attach to the ceramic and metal surfaces. The bonding agent solution is allowed to remain in place for a time sufficient for such displacement and hydrolysis to occur, advantageously from 20 to 30 seconds. Excess solution can be removed by a gentle air blast, and best results with this treatment are by holding the air source at least 6 inches from the surface of the area. The resulting bond appears to be a chemical bond.

Any exposed metal should now be covered with a thin layer of metal opaquer, i.e., the vitreous powder described above with sufficient added pigment, such as titanium dioxide, to provide the desired masking effect, and the layer is sufficient to mask the metal and prevent reflection or translucence. If there is no exposed metal, the step is omitted. In this step, for convenience one heaping scoopful (of the scoop 22 contained in the kit), i.e., about 0.5 ml of the masking powder is mixed with one drop of ethoxylated bisphenol A dimethacrylate resin, or sufficient to wet the powder but to avoid flowing of the mixture. The powder is of a mixture of particle sizes from about 2 to about 95 microns, with about 50% below about 25 microns. The wet mix is applied over any exposed metal 25 in the above-noted thin layer, using a placement instrument or tool 21, which may be provided in the kit 9 as a plastic rod about 4 mm wide, 12 mm long, and 3 to 4 mm thick, and tapered at both ends. The applied coating is allowed to stand for 1 minute to harden.

In the meantime, the restorative material is prepared by mixing one scoopful (using the scoop 22 provided with the kit 9) of vitreous white powder of a mixture of particle sizes between about 2 and about 95 microns, with about 50% less than about 20 microns, with one drop of diluted ethoxylated bisphenol A dimethacrylate resin (or an amount sufficient to wet the powder but so that the mix is just barely too thick to flow). The accelerator in the resin ensures proper setting time and in this instance may be about 0.3% by weight of the resin. The mix is then applied quickly to the damaged area, using a suitable placement instrument, such as the plastic instrument 21 as used above for applying the metal opaquer. To prevent running, it is advantageous to apply it in small quantities. It is also advantageous to slightly overfill the damaged area to allow for proper shaping in the finishing process. The restored area is then allowed to stand until it is set. The restoration mass should not be disturbed during the setting process. The placement must be effected before the mix starts to gel. The restorative material is allowed to stand for about six to seven minutes or until it is set and hardened. It is then shaped and finished with cuttlefish disks and fine diamonds for gross finishing and then finally finished with a rubber wheel or with the conventional finishing paste. To obtain a final smooth surface a thin layer of a conventional glazing agent is applied in the usual way.

FIG. 7 shows another kit 50, also embodying the principles of the invention. It includes a box or container 51, preferably of plastic, fitted with cushioning liners 52 and 53 of foamed plastic or resin, having suitable round recesses or depressions 54 for cylindrical containers, shaped recesses or depressions 55 for bottles, and a tee-shaped depression 56.

The recesses 54 contain (1) a small closed container 60 filled with the priming agent, (2) a similar container 61 filled with the metal opaquer, and (3) a set of similar containers filled with white vitreous powders, differing only in their shades. For example, there may be six different shades of powders, in containers 62, 63, 64, 65, 66, and 67. All of these powders are "white," but there are subtle differences of shades. With these, many shades of teeth or of porcelain can be matched, either directly or by blends. They may be blends of the vitreous material and of pigments. Dark flint silica, a natural material, when blended in different preparations of titanium dioxide gives the full range needed.

The recesses 55 contain (1) a plastic squeeze bottle 70 for the bonding agent, and (2) a plastic squeeze bottle 71 for the resin binder.

The recess 55 contains (1) a couple of plastic mixing tools 72, (2) a scoop 73, and (3) a packet 74 of paper, all as in the kit 9.

Use of the kit 50 is the same as that already described for the kit 9, except that the dentist chooses an appropriate shade of powder or else blends two powders to arrive at the appropriate shade.

The kits 9 and 50 have been designed for the use described, but this does not mean that they are restricted to that use. It can be used for orthodontic bonding to tooth enamel. It can be used to repair bathtubs and other porcelain items.

In the specification and claims, parts and percentages are by weight, unless otherwise indicated, and one drop is equivalent to about 0.05 ml.

As a further indication of feasible particle sizes of the powders (and without any intention of indicating that there is any limitation to the sizes given here), the following information is furnished. A number of batches of powders that are satisfactory were studied. In each of these batches, the minimum particle size diameter was 2.5 microns and the maximum was 95 microns (80 microns in one instance). The proportions of various particle sizes in between 2.5 and 95 microns varied from batch to batch. The weight percents of particles ranged as follows: 80% by weight were below from 26 to 45 microns, median size being 33 microns; 50% by weight ranged from below 14 to 27 microns, median being 18 microns; 20% by weight were below 8 to 14 microns, median being 9.5 microns. The batches contained between 15 and 44 weight percent larger than 30 microns, (median 25%); between 36 and 67 weight percent smaller than 20 microns, (median 55%); and between 1 and 7 weight percent smaller than 5 microns, (median 5%).

What is claimed is:

1. A method of repairing in situ a damaged dental porcelain prosthesis on a suitable base:
   (a) mechanically removing all plaque adjacent the damaged site,
   (b) mechanically removing all friable porcelain at the damaged site,
   (c) washing the damaged site with a priming agent consisting essentially of an aqueous solution of a weak acid,
   (d) removing said agent with a water wash and drying said site,
   (e) applying to the damaged site a bonding agent to adhere a restorative material to said base and to said porcelain and allowing to remain for at least 20 seconds,
   (f) mixing together a liquid resin and white powder in such amounts that the resulting mixture is wet and just barely too thick to flow,
   (g) applying said mixture of resin and powder to at least fill the damaged site and allow to set and harden, and
   (h) finishing the surface of the filled site.

2. The method of claim 1 wherein said priming agent consists essentially of a 30% solution of citric acid in water.

3. The method of claim 1 wherein said bonding agent consists essentially of a butanol solution of gamma-methacryltripropyltrimethoxysilane and gamma-glycidoxypropyltrimethoxysilane, remainder butanol.

4. The method of claim 1 wherein the surface of any exposed metal after step (c) is coated with a mixture of liquid resin and white vitreous powder containing added pigment in sufficient amount to render the mixture opaque, said resin being added in such amount as to wet the powder and avoid flowing of the mixture.

5. The method of claim 4 wherein said admixture contains about 1 part by weight resin and about 3–4 parts by weight of said powder.

6. The method of claim 1 wherein said liquid resin in step (f) is a flowable ethoxylated bisphenol A dimethacrylate resin.

7. The method of claim 1 wherein there are mixed in step (f) about 3–4 parts by weight of white vitreous powder and about 1 part by weight resin.

* * * * *